(12) United States Patent
Henderson et al.

(10) Patent No.: US 10,646,479 B2
(45) Date of Patent: May 12, 2020

(54) USE OF N-(4-IODOBENZOYLAMINO)-5-ETHYL-1,2,3,6-TETRAHYDROPYRIDINE AS A TREATMENT FOR CANCER

(71) Applicant: Florida A&M University, Tallahassee, FL (US)

(72) Inventors: Elizabeth Henderson, Winston-Salem, NC (US); Tiffany Wilson Ardley, Tallahassee, FL (US); Kinfe Ken Redda, Tallahassee, FL (US); Madhavi Gangapuram, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 16/586,328

(22) Filed: Sep. 27, 2019

(65) Prior Publication Data

US 2020/0101052 A1 Apr. 2, 2020

Related U.S. Application Data

(60) Provisional application No. 62/738,386, filed on Sep. 28, 2018.

(51) Int. Cl.
| | | |
|---|---|---|
| *A61K 31/44* | (2006.01) |
| *A61K 31/166* | (2006.01) |
| *A61P 35/00* | (2006.01) |
| *C07D 211/98* | (2006.01) |
| *A61K 31/337* | (2006.01) |
| *A61K 31/7068* | (2006.01) |
| *A61K 31/704* | (2006.01) |
| *A61K 31/4745* | (2006.01) |
| *A61K 31/353* | (2006.01) |
| *A61K 39/395* | (2006.01) |
| *A61K 31/517* | (2006.01) |

(52) U.S. Cl.
CPC ............ *A61K 31/44* (2013.01); *A61K 31/166* (2013.01); *A61K 31/337* (2013.01); *A61K 31/353* (2013.01); *A61K 31/4745* (2013.01); *A61K 31/517* (2013.01); *A61K 31/704* (2013.01); *A61K 31/7068* (2013.01); *A61K 39/3955* (2013.01); *A61P 35/00* (2018.01); *C07D 211/98* (2013.01)

(58) Field of Classification Search
CPC ........ A61K 31/44; A61K 31/166; A61P 35/00
See application file for complete search history.

(56) References Cited

U.S. PATENT DOCUMENTS 4,338,445 A * 7/1982 Knaus .................. C07D 211/70
546/262

* cited by examiner

*Primary Examiner* — Theodore R. West
(74) *Attorney, Agent, or Firm* — Fisherbroyles, LLP; Richard Echler

(57) ABSTRACT

Disclosed herein is the use of N-(4-iodobenzoylamino)-5-ethyl-1,2,3,6-tetra-hydropyridine as a treatment for cancer.

9 Claims, No Drawings

USE OF N-(4-IODOBENZOYLAMINO)-5-ETHYL-1,2,3,6-TETRAHYDROPYRIDINE AS A TREATMENT FOR CANCER

FIELD OF THE DISCLOSURE

Disclosed herein is the use of N-(4-iodobenzoylamino)-5-ethyl-1,2,3,6-tetra-hydropyridine as a treatment for cancer.

BACKGROUND

According to the American Cancer Society, approximately 1,735,350 new cancer cases will be diagnosed and 609,640 cancer deaths in the United States this year. The problems to address are developing targeted therapies and overcoming drug resistances. The status quo as it pertains to tetrahydropyridines as a therapeutic target can be summarized as potential anti-inflammatory agents. Earlier work by Knaus (see, Knaus, E et al., (1976). *Journal of Heterocyclic Chemistry*. 13: 1237) and co-workers indicated the synthesis of a series of N-(carbonylamino)-1,2,3,6-tetrahydropyridines showed anti-inflammatory, analgesic, and hyperglycemic activities with no observed toxicities after preliminary pharmacological tests.

DETAILED DESCRIPTION

The materials, compounds, compositions, articles, and methods described herein may be understood more readily by reference to the following detailed description of specific aspects of the disclosed subject matter and the Examples included therein.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

By "effective amount" as used herein means "an amount of one or more of the disclosed antitumor agents, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of this disclosure can be administered as frequently as necessary to achieve a therapeutic amount.

"Admixture" or "blend" is generally used herein means a physical combination of two or more different components "Excipient" is used herein to include any other compound that may be contained in or combined with one or more of the disclosed inhibitors that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor size or tumor progression). It is understood that this is typically in relation to some standard or expected value, in other words it is relative, but that it is not always necessary for the standard or relative value to be referred to.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, break-down, or eliminate a particular characteristic or event (e.g., tumor size or tumor progression).

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Disclosed herein is the compound N-(4-iodobenzoylamino)-5-ethyl-1,2,3,6-tetrahydropyridine having the formula:

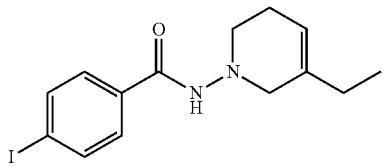 [SMILES: CCC1=CCCN(NC(=O)c2ccc(I)cc2)C1]

which is effective for use in treating cancer.

The disclosed compound can be prepared using the procedures described in Example 1.

Example 1

Ethylacetohydroxamate (10.23 g, 99.20 mmol) was dissolved in 50 mL of N,N-dimethylformamide at 0° C. Fifteen minutes later, mesitylenesulfonyl chloride (21.70 g, 99.20 mmol) was slowly added along with 0.75 mL of triethylamine ($Et_3N$). The solution stirred at ice bath temperature for forty-five minutes. After forty-five minutes, the reaction was poured over ice and a yellow precipitate formed. After the mixture came to room temperature, the solid, ethyl-O-(mesitylenesulfonyl)-acetohydroxamate was collected by vacuum filtration. Ethyl-O-(mesitylenesulfonyl)acetohydroxamate (13.12 g, 45.98 mmol) was washed three times with 100 mL of distilled water and dried for one hour. The product was hydrolyzed with 70% perchloric acid ($HClO_4$) (4 mL) in p-dioxane (14 mL). This reaction stirred for forty-five minutes at 0° C. The reaction was arrested by the addition of ice and an off white solid, mesitylenesulfonyl hydroxamate (MSH) was collected by vacuum filtration and allowed to dry for thirty minutes. MSH (9.00 g, 41.86 mmol) was dissolved in 30 mL of dichloromethane ($CH_2Cl_2$). The reaction stirred at 0° C. for fifteen minutes. 3-ethylpyridine (4.70 mL, 41.86 mmol) was added dropwise and the mixture reacted for forty-five minutes at 0° C. After forty-five minutes, the 3-ethylpyridinium mesitylenesulfonate was extracted with 100 mL of diethyl ether.

3-Ethylpyridinium mesitylenesulfonate (2.00 g, 6.17 mmol) in 30 mL of anhydrous THF at 70° C. was stirred for fifteen minutes before 4-iodobenzoyl chloride (3.29 g, 12.34 mmol) was added. The mixture ran overnight. After twenty-four hours, 10 mL of saturated sodium bicarbonate ($NaHCO_3$) arrested the reaction. The product, N-(4-Iodobenzoylimino)-5-ethylpyridinium ylide (EH-1-23) was extracted with 100 mL of $CH_2Cl_2$ three times and dried over sodium sulfate. The ylide was obtained by filtration and evaporation of the solvent, then purified by flash column chromatography using ethyl acetate and methanol (9:1). The result (EH-1-23) was a white solid (1.25 g, 63%); mp: 125.2-127.0° C.; $^1$H-NMR (300 MHz $CDCl_3$) (δ): 1.21 (t, J=7.5 Hz, $CH_2CH_3$, 3H), 2.92 (q, J=7.6 Hz, $CH_2CH_3$, 2H), 7.65 (dd, J=8.7, 2.0 Hz, $C_{2'}$, $C_{6'}$—H, 2H), 7.72-7.86 (m, $C_{3'}$, $C_{5'}$—H, 2H), 7.97 (t, J=7.1 Hz, $C_5$—H, 1H), 8.27 (d, J=7.6 Hz, $C_4$—H, 1H), 8.82-8.96 (m, $C_2$, $C_6$—H, 2H).

Sodium borohydride (1.34 g, 17.75 mmol) was added to a solution of (EH-1-23) (1.25 g, 3.55 mmol) in 30 mL of absolute ethanol at 0° C. The reaction stirred for seven hours and was monitored by thin layer chromatography (TLC). The reaction was arrested with ice and allowed to warm to room temperature. The compound, N-(4-Iodobenzoylamino)-3-ethyl-1,2,3,6-tetrahydropyridine (EH-1-40) was extracted with dichloromethane (3×100 mL). The combined extracts were dried over sodium sulfate ($Na_2SO_4$), filtered, and rotoevaporated. The solid obtained was purified by flash column chromatography using ethyl acetate and hexane (6:4). Rotoevaporation gave a white solid (0.07 g, 0.20 mmol); mp: 174.5-177.5° C.; IR (potassium bromide): υ 3180 (NH), 1669 (CO) $cm^{-1}$; $^1$H-NMR (300 MHz $CDCl_3$) (δ): 1.02 (t, J=7.5 Hz, $CH_2CH_3$, 3H), 1.93-1.98 (q, J=6.9, 7.8 Hz, $CH_2CH_3$, 2H), 3.07 (t, J=5.8 Hz, $C_5$—H, 2H), 3.41 (s, $C_2$, $C_6$—H, 2H), 5.50 (s, 1H, $C_4$—H), 7.01 (s, 1H, NH), 7.46 (d, J=8.3 Hz, $C_{2'}$, $C_{6'}$—H, 2H), 7.78 (d, J=8.4 Hz, $C_{3'}$, $C_{5'}$—H, 2H), 7.01 (s, NH, D2O Exchange); $^{13}$C-NMR (150 MHz $CDCl_3$) (δ): 11.73 ($CH_2CH_3$), 23.71 ($C_5$), 27.33 ($CH_2CH_3$), 52.30 ($C_6$), 56.38 ($C_2$), 100.0 ($C_{4'}$), 117.25 ($C_4$), 129.18 ($C_{2'}$, $C_{6'}$), 134.68 ($C_3$), 137.98 ($C_{3'}$, $C_{5'}$), 165.24 (C=O).

Methods

Disclosed herein is a method for treating cancer in a subject, comprising contacting the subject with an effective amount of N-(4-iodobenzoylamino)-5-ethyl-1,2,3,6-tetrahydro-pyridine.

This compound was evaluated against three types of cancer cells: Ishikawa, MDA-MB-231, and MCF-7 using the CellTiter-Glo (CTG) luminescent cell viability assay.

Ishikawa cell line is an endometrial adenocarcinoma isolated from a 39-year-old female. MDA-MB-231 is a triple negative breast cancer cell line isolated from a 50-year-old Caucasian female. MCF-7 is an estrogen receptor positive breast cancer cell line isolated from a 69-year-old Caucasian female. Table 1 provides the $IC_{50}$ values of the present compound, Tamoxifen, and 4-hydroxytamoxifen on Ishikawa, MCF-7, and MDA-MB-231 cell lines. Tamoxifen is a selective estrogen receptor modulator (SERM). 4-Hydroxytamoxifen is an active metabolite of Tamoxifen. The $IC_{50}$ values for N-(4-iodobenzoylamino)-5-ethyl-1,2,3,6-tetrahydropyridines (EH-1-40) are 2.932 µM (Ishikawa cells), 1.25 µM (MCF-7), and 5.67 µM (MDA-MB-231). EH-1-40 exhibited better activity on Ishikawa, MCF-7, and MDA-MB-231 cell lines compared to Tamoxifen and 4-Hydroxtamnxifen.

TABLE I

| TEST COMPOUND | $IC_{50}$ (µM) | | |
|---|---|---|---|
| | ISHIKAWA | MCF-7 | MDA-MB-231 |
| 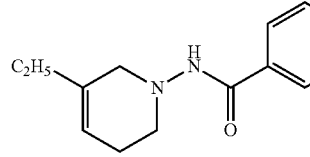 | 2.932 | 1.25 | 5.67 |
| Tamoxifen | 29.89 | 26.97 | 29.40 |
| 4-Hydroxytamoxifen | 26.35 | 6.78 | 23.07 |

Disclosed herein is a method for treating cancer in a subject, comprising contacting the subject with an effective amount of N-(4-iodobenzoylamino)-5-ethyl-1,2,3,6-tetrahydro-pyridine.

The disclosed compound can be used to prevent, abate, minimize, control, and/or lessen tumor metastasis in humans and animals. The disclosed compound can also be used to slow the rate of primary tumor growth. The disclosed compound when administered to a subject in need of treatment can be used to stop the spread of cancer cells. As such, the compound disclosed herein can be administered as part of a combination therapy with one or more drugs or other pharmaceutical agents. When used as part of the combination therapy, the decrease in metastasis and reduction in primary tumor growth afforded by the disclosed compounds allows for a more effective and efficient use of any pharmaceutical or drug therapy being used to treat the patient. In addition, control of metastasis by the disclosed compound affords the subject a greater ability to concentrate the disease in one location.

Disclosed herein are methods for preventing metastasis of malignant tumors or other cancerous cells as well as to reduce the rate of tumor growth. The methods comprise administering an effective amount of the disclosed compound to a subject diagnosed with a malignant tumor or cancerous cells or to a subject having a tumor or cancerous cells.

Further disclosed herein is the use of the disclosed compound for making a medicament for preventing metastasis of malignant tumors or other cancerous cells and for slowing tumor growth.

The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytoma/Malignant Glioma; Craniopharyngioma; Ependymoblastoma; Ependymoma; Medulloblastoma; Medulloepithelioma; Pineal Parenchymal Tumors of Intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma; Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; Intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenström; Malignant Fibrous Histiocytoma of Bone and Osteosarcoma; Medulloblastoma; Melanoma; Melanoma, Intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis Fungoides; Myelodysplastic Syndromes; Myelodysplastic/-Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Cell Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sézary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenström Macroglobulinemia; and Wilms Tumor.

Also disclosed herein is a method for treating a subject diagnosed with cancer, comprising administering to the subject an effective amount of one or more of the disclosed compounds.

Further disclosed herein is a method for treating carcinoma in a subject, comprising administering to the subject having a carcinoma a composition comprising:
  a) an effective amount of N-(4-iodobenzoylamino)-5-ethyl-1,2,3,6-tetrahydro-pyridine; and
  b) an effective amount of a chemotherapeutic agent.

Still further disclosed herein is a method for treating carcinoma in a subject, comprising administering to the subject having a carcinoma a composition comprising:
  a) an effective amount of N-(4-iodobenzoylamino)-5-ethyl-1,2,3,6-tetrahydro-pyridine; and
  b) an effective amount of a compound that inhibits tumor growth.

Disclosed herein is the use of N-(4-iodobenzoylamino)-5-ethyl-1,2,3,6-tetrahydro-pyridine for making a medicament for treating carcinoma.

Disclosed herein is the use of N-(4-iodobenzoylamino)-5-ethyl-1,2,3,6-tetrahydro-pyridine for making a medicament for treating malignant tumors.

Disclosed herein is the use of N-(4-iodobenzoylamino)-5-ethyl-1,2,3,6-tetrahydro-pyridine for making a medicament for reducing the volume of tumors in a subject having malignant tumors.

Compositions

Disclosed herein are compositions which can be used to prevent metastasis of cancer cells in a subject, the compositions comprising an effective amount of N-(4-iodobenzoylamino)-5-ethyl-1,2,3,6-tetrahydropyridine. Further disclosed herein are compositions that can be used to treat tumors in a human or other mammal.

One aspect relates to a composition comprising:
  a) an effective amount of N-(4-iodobenzoylamino)-5-ethyl-1,2,3,6-tetrahydro-pyridine; and
  b) one or more pharmaceutically acceptable ingredients.

Another aspect relates a composition comprising:
  a) an effective amount of N-(4-iodobenzoylamino)-5-ethyl-1,2,3,6-tetrahydro-pyridine; and
  b) an effective amount of one or chemotherapeutic agents;
  wherein the disclosed compounds and the chemotherapeutic agents can be administered together or in any order.

One embodiment relates to a composition comprising:
  a) an effective amount of N-(4-iodobenzoylamino)-5-ethyl-1,2,3,6-tetrahydro-pyridine; and
  b) an effective amount of taxol;
  wherein the disclosed compounds and taxol can be administered together or in any order.

Another embodiment relates to a composition comprising:
  a) an effective amount of N-(4-iodobenzoylamino)-5-ethyl-1,2,3,6-tetrahydro-pyridine; and
  b) an effective amount of gemcitabine;
  wherein the disclosed compounds and gemcitabine can be administered together or in any order.

A further embodiment relate to a composition comprising:
  a) an effective amount of N-(4-iodobenzoylamino)-5-ethyl-1,2,3,6-tetrahydro-pyridine; and
  b) an effective amount of erlotinib;
  wherein the disclosed compounds and erlotinib can be administered together or in any order.

A yet further embodiment relate to a composition comprising:
  a) an effective amount of N-(4-iodobenzoylamino)-5-ethyl-1,2,3,6-tetrahydro-pyridine; and
  b) an effective amount of doxil;
  wherein the disclosed compounds and doxil can be administered together or in any order.

A still further embodiment relate to a composition comprising:
  a) an effective amount of N-(4-iodobenzoylamino)-5-ethyl-1,2,3,6-tetrahydro-pyridine; and
  b) an effective amount of irinortecan;
  wherein the disclosed compounds and irinortecan can be administered together or in any order.

A still yet further embodiment relate to a composition comprising:
  a) an effective amount of N-(4-iodobenzoylamino)-5-ethyl-1,2,3,6-tetrahydro-pyridine; and
  b) an effective amount of bevacizumab;
  wherein the disclosed compounds and bevacizumab can be administered together or in any order.

A still yet another further embodiment relate to a composition comprising:
  a) an effective amount of N-(4-iodobenzoylamino)-5-ethyl-1,2,3,6-tetrahydro-pyridine; and
  b) an effective amount of flavopiridol;
  wherein the disclosed compounds and flavopiridol can be administered together or in any order.

The targeted cells, i.e., cancer cells or tumor can be contacted with an aqueous solution comprising from about 0.5 µM to about 250 µM of N-(4-iodobenzoylamino)-5-ethyl-1,2,3,6-tetrahydropyridine. In one embodiment the compositions can comprise from about 1 µM to about 100 µM of N-(4-iodobenzoylamino)-5-ethyl-1,2,3,6-tetrahydropyridine. In another embodiment the compositions can comprise from about 10 µM to about 100 µM N-(4-iodobenzoylamino)-5-ethyl-1,2,3,6-tetrahydropyridine. In a further embodiment the compositions can comprise from about 5 µM to about 20 µM N-(4-iodobenzoylamino)-5-ethyl-1,2,3,6-tetrahydropyridine. In a yet further embodiment the compositions can comprise from about 1 µM to about 50 µM N-(4-iodobenzoylamino)-5-ethyl-1,2,3,6-tetrahydropyridine. In a yet another embodiment the compositions can comprise from about 1 µM to about 10 µM N-(4-iodobenzoylamino)-5-ethyl-1,2,3,6-tetrahydropyridine. In a still further embodiment the compositions can comprise from about 15 µM to about 50 µM N-(4-iodobenzoylamino)-5-ethyl-1,2,3,6-tetrahydropyridine. In still another embodiment the compositions can comprise from about 20 µM to about 200 µM N-(4-iodobenzoylamino)-5-ethyl-1,2,3,6-tetrahydropyridine.

The compositions can comprise any amount of N-(4-iodobenzoylamino)-5-ethyl-1,2,3,6-tetrahydropyridine from about 0.5 µM to about 250 µM, for example, 1 µM, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 22 µM, 22 µM, 23 µM, 24 µM, 25 µM, 26 µM, 27 µM, 28 µM, 29 µM, 30 µM, 31 µM, 32 µM, 33 µM, 34 µM, 35 µM, 36 µM, 37 µM, 38 µM, 39 µM, 40 µM, 41 µM, 42 µM, 43 µM, 44 µM, 45 µM, 46 µM, 47 µM, 48 µM, 49 µM, 50 µM, 51 µM, 52 µM, 53 µM, 54 µM, 55 µM, 56 µM, 57 µM, 58 µM, 59 µM, 60 µM, 61 µM, 62 µM, 63 µM, 64 µM, 65 µM, 66 µM, 67 µM, 68 µM, 69 µM, 70 µM, 71 µM, 72 µM, 73 µM, 74 µM, 75 µM, 76 µM, 77 µM, 78 µM, 79 µM, 80 µM, 81 µM, 82 µM, 83 µM, 84 µM, 85 µM, 86 µM, 87 µM, 88 µM, 89 µM, 90 µM, 91 µM, 92 µM, 93 µM, 94 µM, 95 µM, 96 µM, 97 µM, 98 µM, 99 µM and 100 µM.

A "chemotherapeutic agent" or "chemotherapeutic compound" is a chemical compound useful in the treatment of cancer. Chemotherapeutic cancer agents that can be used in combination with N-(4-iodobenzoylamino)-5-ethyl-1,2,3,6-tetrahydropyridine, but are not limited to, mitotic inhibitors (vinca alkaloids). These include vincristine, vinblastine, vindesine and Navelbine™ (vinorelbine-5'-noranhydroblastine). In yet other embodiments, chemotherapeutic cancer agents include topoisomerase I inhibitors, such as camptothecin compounds. As used herein, "camptothecin compounds" include Camptosar™ (irinotecan HCL), Hycamtin™ (topotecan HCL) and other compounds derived from camptothecin and its analogues. Another category of chemotherapeutic cancer agents that may be used in the methods and compositions of the present disclosure are podophyllotoxin derivatives, such as etoposide, teniposide and mitopodozide. The present disclosure further encompasses other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin, and dacarbazine. The present disclosure encompasses antimetabolites as chemotherapeutic agents. Examples of these types of agents include cytosine arabinoside, fluorouracil, methotrexate, mercaptopurine, azathioprime, and procarbazine. An additional category of chemotherapeutic cancer agents that may be used in the methods and compositions of the present disclosure include antibiotics. Examples include without limitation doxorubicin, bleomycin, dactinomycin, daunorubicin, mithramycin, mitomycin, mytomycin C, and daunomycin. There are numerous liposomal formulations commercially available for these compounds. The present disclosure further encompasses other chemotherapeutic cancer agents including without limitation anti-tumor antibodies, dacarbazine, azacytidine, amsacrine, melphalan, ifosfamide and mitoxantrone.

The N-(4-iodobenzoylamino)-5-ethyl-1,2,3,6-tetrahydropyridine can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with N-(4-iodobenzoylamino)-5-ethyl-1,2,3,6-tetrahydropyridine include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

The term "effective amount" as used herein means "an amount of one or more phenylsulfamic acids, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. Thus, it is not possible to specify an exact "effective amount." For example, several divided doses may be administered daily or the dose may be proportionally reduced as indicated by the exigencies of the therapeutic situation. In addition, the compositions of the present disclosure can be administered as frequently as necessary to achieve a therapeutic amount.

Disclosed herein is a medicament comprising one or more compounds disclosed herein. Disclosed herein is the use of a disclosed compound for making a medicament suitable for use in reducing tumor volume.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure

What is claimed is:

1. A compound having the formula:

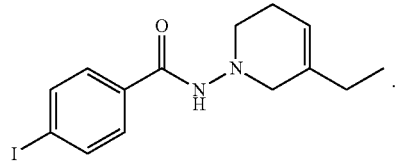 [SMILES: CCC1=CCCN(NC(=O)c2ccc(I)cc2)C1]

2. A compound that is identified by the following spectroscopic measurements:
   a) $^1$H NMR spectrum having the following chemical shifts at 300 MHz in CDCl$_3$ (δ): 1.02 (t, J=7.5 Hz, CH$_2$CH$_3$, 3H), 1.93-1.98 (q, J=6.9, 7.8 Hz, CH$_2$CH$_3$, 2H), 3.07 (t, J=5.8 Hz, C$_5$—H, 2H), 3.41 (s, C$_2$, C$_6$—H, 2H), 5.50 (s, 1H, C$_4$—H), 7.01 (s, 1H, NH), 7.46 (d, J=8.3 Hz, C$_{2'}$, C$_{6'}$—H, 2H), 7.78 (d, J=8.4 Hz, C$_{3'}$, C$_{5'}$—H, 2H); and
   b) $^{13}$C NMR spectrum having the following chemical shifts at 150 MHz in CDCl$_3$ (δ): 11.73 (CH$_2$CH$_3$), 23.71 (C$_5$), 27.33 (CH$_2$CH$_3$), 52.30 (C$_6$), 56.38 (C$_2$), 100.0 (C$_{4'}$), 117.25 (C$_4$), 129.18 (C$_{2'}$, C$_{6'}$), 134.68 (C$_3$), 137.98 (C$_{3'}$, C$_{5'}$), 165.24 (C=O).

3. A method for treating cancer comprising administering to a subject in need thereof an effective amount of N-(4-iodobenzoylamino)-3-ethyl-1,2,3,6-tetrahydropyridine having the formula:

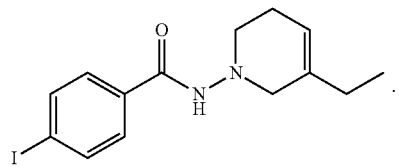 [SMILES: CCC1=CCCN(NC(=O)c2ccc(I)cc2)C1]

4. The method according to claim 3, wherein the cancer is chosen from endometrial adenocarcinoma and breast cancer.

5. A method for treating cancer comprising administering to a subject in need thereof a composition, comprising:
   a) an effective amount of N-(4-iodobenzoylamino)-3-ethyl-1,2,3,6-tetrahydropyridine having the formula:

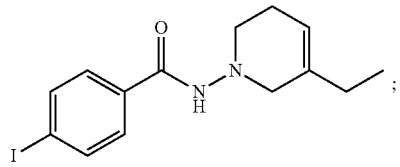 [SMILES: CCC1=CCCN(NC(=O)c2ccc(I)cc2)C1]

and
   b) one or more anti-cancer agents chosen from taxol, gemcitabine, erlotinib, doxil, irinortecan, bevacizumab, flavopiridol, and mixtures thereof.

6. The method according to claim 5, wherein the cancer is chosen from endometrial adenocarcinoma and breast cancer.

7. The method according to claim 5, wherein the composition comprises from about 0.1 μM to about 20 μM of N-(4-iodobenzoyl-amino)-3-ethyl-1,2,3,6-tetrahydropyridine.

8. A composition for treating cancer, comprising:
   a) from about 0.1 μM to about 20 μM of N-(4-iodobenzoyl-amino)-3-ethyl-1,2,3,6-tetrahydropyridine; and
   b) one or more pharmaceutically acceptable ingredients or agents.

9. The composition according to claim 8, wherein the cancer is chosen from endometrial adenocarcinoma and breast cancer.

* * * * *